US00PP21423P2

(12) United States Plant Patent
van Marrewijk

(10) Patent No.: US PP21,423 P2
(45) Date of Patent: Oct. 26, 2010

(54) *PETUNIA* PLANT NAMED 'PETPRE01'

(50) Latin Name: ***Petunia integrifolia* spp. *inflata* spp. *thymifolia***
Varietal Denomination: PETPRE01

(76) Inventor: Wim van Marrewijk, Laan van Vijverberg 15, PO Box 374, Naaldwijk (NL) 2670

( * ) Notice: Subject to any disclaimer, the term of this patent is extended or adjusted under 35 U.S.C. 154(b) by 0 days.

(21) Appl. No.: 12/460,360

(22) Filed: Jul. 18, 2009

(51) Int. Cl.
*A01H 5/00* (2006.01)

(52) U.S. Cl. ..... Plt./356
(58) Field of Classification Search ..... Plt./356
See application file for complete search history.

*Primary Examiner*—Kent L Bell

(57) ABSTRACT

A new and distinct *Petunia* cultivar named 'PetPre01' is disclosed, characterized by having a dense, mat forming plant, small, semi-double flowers and dense, non-sticky foliage. Additionally, the new variety shows excellent tolerance to drought conditions, showing no negative effects at 50% of the water consumption of typical, similar *Petunia* varieties known to the inventor. The new variety is a *Petunia,* normally produced as an outdoor garden or container plant.

1 Drawing Sheet

Figure 1:
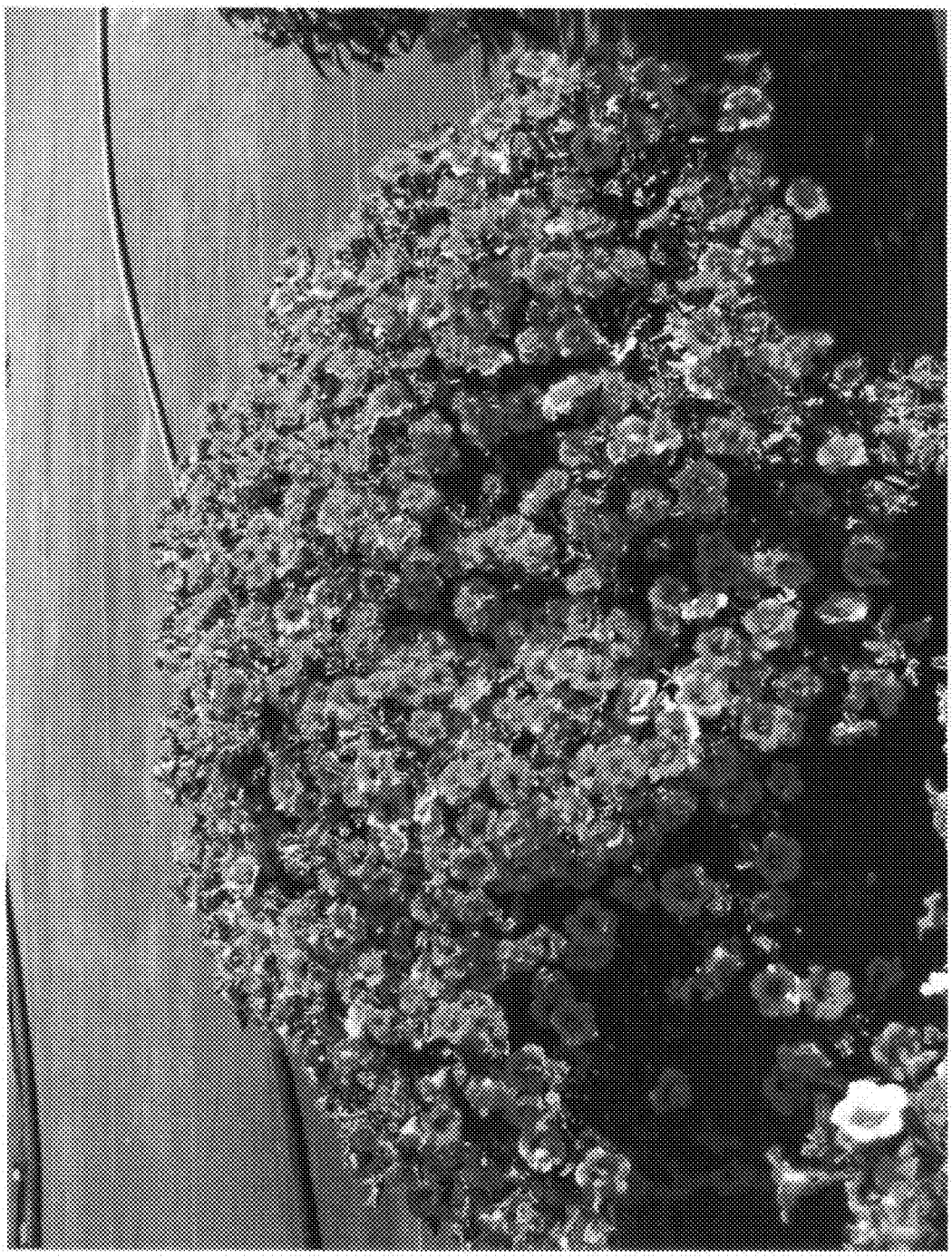

Latin name of the genus and species: *Petunia integrifolia* spp. inflata spp. *thymifolia.*

Variety denomination: 'PETPRE01'.

BACKGROUND OF THE INVENTION

The new *Petunia* cultivar is a product of a planned breeding program conducted by the inventor, Wim van Marrewijk, in the Netherlands. The objective of the breeding program was to produce drought tolerant varieties of *Petunia* for commercial introduction. The seed parent is an unpatented, unnamed, proprietary seedling of *Petunia integrifolia* spp. *inflata.* The pollen parent is an unpatented, unnamed proprietary seedling of *Petunia thymifolia.* The crossing was performed during May 2001.

In April 2002, the new variety was discovered and selected by the inventor in a group of seedlings resulting from that crossing, in a commercial greenhouse in the Netherlands. Asexual reproduction of the new cultivar 'PETPRE01' by vegetative cuttings was first performed at a commercial greenhouse in the Netherlands in April 2002. Subsequent asexual propagation has shown that the unique features of this cultivar are stable and reproduced true to type on successive generations.

SUMMARY OF THE INVENTION

The cultivar 'PETPRE01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PETPRE01' These characteristics in combination distinguish 'PETPRE01' as a new and distinct *Petunia* cultivar:

1. Dense, mat forming plant.
2. Small, semi-double to double flowers.
3. Low water requirements, approximately 50% of similar *Petunia* varieties known to the inventor.
4. Dense, non-sticky foliage.

PARENTAL COMPARISON

Plants of the new cultivar 'PETPRE01' are similar to plants of the seed parent, *Petunia integrifolia* spp. *inflata* in most horticultural characteristics, however, plants of the new cultivar 'PETPRE01' have a flatter, more matte forming growth habit, and double to semi-double flowers, compared to the single flowers of the seed parent.

Plants of the new cultivar 'PETPRE01' are similar to plants of the pollen parent, *Petunia thymifolia* in most horticultural characteristics, however, plants of the new cultivar 'PETPRE01' are faster growing, with significantly larger foliage.

COMMERCIAL COMPARISON

The inventor is not aware of similar drought tolerant *Petunia* varieties to make a meaningful comparison with.

BRIEF DESCRIPTION OF THE PHOTOGRAPH

The accompanying photograph in FIG. 1 illustrates in full color a typical plant of 'PETPRE01' grown in a greenhouse, in a 30 cm pot. Age of the plant photographed is approximately 4 months from a rooted cutting. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'PETPRE01' plants grown in a commercial greenhouse, in Encinitas, Calif. during the Spring. The growing temperature ranged from 17° C. to 23° C. during the night and 20° C. to 35° C. during the day. Light conditions were bright, high sunlight conditions. Measurements and numerical values represent averages of typical plant types.

Botanical classification: *Petunia integrifolia* ssp. *inflata*× *thymifolia*. 'PetPre01'.

PROPAGATION

Time to initiate roots: 10 to 14 days at approximately 18-35 ° C.
Root description: Fibrous

PLANT

Growth habit: Dense, mat forming. Initially flat spreading, then, mounding.
Pot size of plant described: Approximately 16 cm.
Height: To top of flowers: Approximately 20 to 25 cm.
Plant spread: Approximately 50 cm, mature 1 year old plant.
Growth rate: Moderate.
Branching characteristics: Very free branching.
Characteristics of primary lateral branches:
*Diameter.*—Approximately 0.2 cm.
*Color.*—Near RHS Green 143C.
*Texture.*—Very lightly pubescent.
*Strength.*—Flexible and very strong.
Internodes length: Average 1-2.5 cm.

FOLIAGE

Leaf:
*Arrangement.*—Opposite.
*Quantity.*—Approximately 40 leaves per branch.
*Average length.*—3 to 4 cm.
*Average width.*—2.5 to 3.0 cm.
*Shape of blade.*—Ovate.
*Apex.*—Acute.
*Base.*—Acute.
*Margin.*—Entire.
*Texture of top surface.*—Glabrous.
*Pubescence.*—Pubescent.
*Aspect.*—90 degrees.
*Color.*—Young foliage upper side: Near RHS Green 137 A. Young foliage under side: Near RHS Green 137 A. Mature foliage upper side: Near RHS Green 137 A. Mature foliage under side: Near RHS Green 137 A.
Venation:
*Type.*—Pinnate.
*Venation color upper side.*—Near RHS Green N138B.
*Venation color under side.*—Near RHS Green N138B.
Petiole: No Petiole.

FLOWER

Natural flowering season: Spring, summer and autumn.
Days to flowering from rooted cutting: Average 7 to 10 weeks.
Inflorescence and flower type and habit: Terminal, double, salverform.
Flower longevity on plant: Individual flowers last approximately 1 week without significant degradation or color loss.
Persistent or self-cleaning: self-cleaning.
Bud:
*Shape.*—Ovate.
*Length.*—1.0 cm.
*Diameter.*—0.5 cm.
*Color.*—Near RHS purple N79 A.
Flower size:
*Diameter.*—Approximately 3.5 cm.
*Flower tube length.*—Approximately 1.5 cm.
Petals:
*Length from throat.*—Approximately 1.2 cm.
*Width.*—Approximately 1 cm.
*Quantity.*—8 to 12.
*Texture.*—Smooth.
*Apex.*—Blunt.
*Margin.*—Entire.
Color: When opening: Upper surface: Near RHS Red-Purple N78A. Lower surface: Near RHS Red-Purple N78B. Fully opened: Upper surface: Near RHS Red-Purple N74 A. Lower surface: Near RHS Red-Purple-Violet N81B. Fading: Upper surface: Near RHS Red-Purple N74 D. Lower surface: Near RHS Red-Purple-Violet N81D.
Calyx/Sepals:
*Quantity per flower.*—5.
*Shape.*—Elliptic.
*Length.*—Approximately 0.6 cm.
*Width.*—Approximately 0.2 cm.
*Apex.*—Acute.
*Base.*—Cuneate.
*Margin.*—Entire.
*Texture.*—Matte.
*Color.*—Upper surface: Near RHS green 137 A. Lower surface: Near RHS green 137 A.
Pedicel:
*Length.*—Approximately 1.5 cm.
*Diameter.*—Approximately 0.1 cm.
*Color.*—Near RHS green 137 A.
*Texture.*—Strigose.
Fragrance: Moderate.

REPRODUCTIVE ORGANS

Stamens:
*Number.*—5.
*Filament length.*—Approximately 0.9 cm.
Anthers: Length: Approximately 0.1 cm. Shape: Round. Color: Dark purple. Pollen: Color: White. Quantity: Profuse.
Pistil:
*Number.*—1.
*Length.*—Approximately 0.7 cm.
*Style.*—Length: Approximately 0.7 cm. Color: Light purple.
*Stigma.*—Shape: globular. Color: Near RHS Green 139 D. Ovary Color: Near RHS Green 139 D.

OTHER CHARACTERISTICS

Seeds and fruits: Not observed.
Disease/pest resistance: Neither resistant nor susceptible to normal diseases and pests of *Petunia*.
Temperature tolerance: Tolerates low temperatures to 3° C. Upper temperatures to 52° C. if given water. Without supplemental water, upper temperature tolerance to 40° C.
Drought tolerance: Excellent drought tolerance. Compared to commercial varieties known to the inventor, 'PetPre01' can tolerate 50% of water quantity, without any negative effects.

What is claimed is:

1. A new and distinct cultivar of *Petunia* plant named 'PETPRE01' as herein illustrated and described.

* * * * *